United States Patent
Tai et al.

(10) Patent No.: US 11,318,225 B2
(45) Date of Patent: *May 3, 2022

(54) ULTRATHIN PARYLENE-C SEMIPERMEABLE MEMBRANES FOR BIOMEDICAL APPLICATIONS

(71) Applicants: California Institute of Technology, Pasadena, CA (US); University of Southern California, Los Angeles, CA (US)

(72) Inventors: Yu-Chong Tai, Pasadena, CA (US); Bo Lu, Pasadena, CA (US); Mark Humayun, Glendale, CA (US)

(73) Assignees: California Institute of Technology, Pasadena, CA (US); University of Southern California, Los Anaeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/184,934

(22) Filed: Jun. 16, 2016

(65) Prior Publication Data

US 2016/0361463 A1    Dec. 15, 2016

Related U.S. Application Data

(63) Continuation of application No. 14/498,918, filed on Sep. 26, 2014, now abandoned, which is a continuation of application No. 13/355,426, filed on Jan. 20, 2012, now Pat. No. 8,877,489, application No. 15/184,934, which is a continuation of application No. 14/314,994, filed on Jun. 25, 2014.

(60) Provisional application No. 61/566,965, filed on Dec. 5, 2011.

(51) Int. Cl.
| | |
|---|---|
| *C12N 5/00* | (2006.01) |
| *A61L 27/16* | (2006.01) |
| *B01D 71/44* | (2006.01) |
| *A61L 27/50* | (2006.01) |
| *A61L 27/56* | (2006.01) |

(52) U.S. Cl.
CPC ............ *A61L 27/16* (2013.01); *A61L 27/50* (2013.01); *A61L 27/56* (2013.01); *B01D 71/44* (2013.01); *C12N 5/0068* (2013.01); *A61L 2430/16* (2013.01); *B01D 2325/06* (2013.01); *C12N 2533/30* (2013.01); *C12N 2535/10* (2013.01); *C12N 2539/00* (2013.01)

(58) Field of Classification Search
CPC ............ C12N 5/0068; C12N 2539/00; C12N 2535/10; C12N 2533/30; A61L 2430/16; A61L 27/56
See application file for complete search history.

(56) References Cited

U.S. PATENT DOCUMENTS

| | | | |
|---|---|---|---|
| 4,047,532 A | 9/1977 | Phillips et al. |
| 4,700,298 A | 10/1987 | Palcic et al. |
| 4,715,373 A | 12/1987 | Mazzocco et al. |
| 5,024,223 A | 6/1991 | Chow |
| 5,196,003 A | 3/1993 | Bilweis |
| 5,688,264 A | 11/1997 | Simon et al. |
| 5,843,780 A | 12/1998 | Thomson et al. |
| 6,117,675 A | 9/2000 | Van Der et al. |
| 6,156,042 A | 12/2000 | Aramant et al. |
| 6,200,806 B1 | 3/2001 | Thomson |
| 6,231,879 B1 | 5/2001 | Li et al. |
| 6,254,628 B1 | 7/2001 | Wallace et al. |
| 6,264,941 B1 | 7/2001 | Baetge et al. |
| 6,299,895 B1 | 10/2001 | Hammang et al. |
| 6,303,136 B1 | 10/2001 | Li et al. |
| 6,322,804 B1 | 11/2001 | Dionne et al. |
| 6,337,198 B1 | 1/2002 | Levene et al. |
| 6,361,771 B1 | 3/2002 | Tao et al. |
| 6,436,427 B1 | 8/2002 | Hammang et al. |
| 6,582,903 B1 | 6/2003 | Rigler et al. |
| 6,627,422 B1 | 9/2003 | Li et al. |

(Continued)

FOREIGN PATENT DOCUMENTS

| | | |
|---|---|---|
| AU | 2011279250 | 3/2015 |
| EP | 1806524 | 7/2007 |

(Continued)

OTHER PUBLICATIONS

Fortin et al., A Model for the Chemical Vapor Deposition of Poly9para-xylylene) (Parylene) Thin Fimls, Chem. Mater. 2002, 14, 1945-1949.*

Giacchino et al. Parylene-Membrane Piezoresistive Pressure Sensors With XEF2-etched Cavity; Sensors, IEEE Conference, pp. 1568-1571. (Year: 2008).*

(Continued)

*Primary Examiner* — Susan M Hanley
*Assistant Examiner* — Paul C Martin
(74) *Attorney, Agent, or Firm* — Kilpatrick Townsend & Stockton LLP

(57) ABSTRACT

Thin parylene C membranes having smooth front sides and ultrathin regions (e.g., 0.01 μm to 5 μm thick) interspersed with thicker regions are disclosed. The back sides of the membranes can be rough compared with the smooth front sides. The membranes can be used in vitro to grow monolayers of cells in a laboratory or in vivo as surgically implantable growth layers, such as to replace the Bruch's membrane in the eye. The thin regions of parylene are semipermeable to allow for proteins in serum to pass through, and the thick regions give mechanical support for handling by a surgeon. The smooth front side allows for monolayer cell growth, and the rough back side helps prevents cells from attaching there.

20 Claims, 9 Drawing Sheets

(56) References Cited

U.S. PATENT DOCUMENTS

| | | | |
|---|---|---|---|
| 6,642,048 B2 | 11/2003 | Xu et al. |
| 6,649,184 B2 | 11/2003 | Hammang et al. |
| 6,667,176 B1 | 12/2003 | Funk et al. |
| 6,669,719 B2 | 12/2003 | Wallace et al. |
| 6,712,837 B2 | 3/2004 | Akerfeldt et al. |
| 6,800,480 B1 | 10/2004 | Bodnar et al. |
| 6,833,269 B2 | 12/2004 | Carpenter et al. |
| 6,852,527 B2 | 2/2005 | Chan et al. |
| 6,875,607 B1 | 4/2005 | Reubinoff et al. |
| 6,939,378 B2 | 9/2005 | Fishman et al. |
| 6,942,873 B2 | 9/2005 | Russell et al. |
| 7,005,252 B1 | 2/2006 | Thomson |
| 7,011,828 B2 | 3/2006 | Reubinoff et al. |
| 7,029,913 B2 | 4/2006 | Thomson et al. |
| 7,107,124 B2 | 9/2006 | Green |
| 7,115,257 B1 | 10/2006 | Tao et al. |
| 7,135,172 B1 | 11/2006 | Loftus et al. |
| 7,141,369 B2 | 11/2006 | Cao |
| 7,147,648 B2 | 12/2006 | Lin |
| 7,217,569 B2 | 5/2007 | Thomson |
| 7,250,294 B2 | 7/2007 | Carpenter et al. |
| 7,297,539 B2 | 11/2007 | Mandalam et al. |
| 7,384,426 B2 | 6/2008 | Wallace et al. |
| 7,410,798 B2 | 8/2008 | Mandalam et al. |
| 7,413,734 B2 | 8/2008 | Mistry et al. |
| 7,413,902 B2 | 8/2008 | Bodnar et al. |
| 7,439,064 B2 | 10/2008 | Thomson et al. |
| 7,455,983 B2 | 11/2008 | Xu et al. |
| 7,504,257 B2 | 3/2009 | Reubinoff et al. |
| 7,541,186 B2 | 6/2009 | Reh et al. |
| 7,582,479 B2 | 9/2009 | Thomson et al. |
| 7,601,525 B2 | 10/2009 | Batich et al. |
| 7,604,992 B2 | 10/2009 | Reubinoff |
| 7,695,967 B1 | 4/2010 | Russell et al. |
| 7,736,896 B2 | 6/2010 | Klimanskaya et al. |
| 7,749,726 B2 | 7/2010 | Chuck et al. |
| 7,781,216 B2 | 8/2010 | Thomson |
| 7,794,704 B2 | 9/2010 | Klimanskaya et al. |
| 7,795,025 B2 | 9/2010 | Klimanskaya et al. |
| 7,820,195 B2 | 10/2010 | Kauper et al. |
| 7,824,671 B2 | 11/2010 | Binder et al. |
| 7,838,727 B2 | 11/2010 | Lanza et al. |
| 7,846,467 B2 | 12/2010 | Coroneo et al. |
| 7,855,068 B2 | 12/2010 | Cao |
| 7,875,296 B2 | 1/2011 | Binette et al. |
| 7,893,315 B2 | 2/2011 | Chung et al. |
| 7,910,369 B2 | 3/2011 | West et al. |
| 7,914,147 B2 | 3/2011 | Sharifzadeh et al. |
| 7,947,498 B2 | 5/2011 | Reubinoff et al. |
| 7,959,942 B2 | 6/2011 | Cottone |
| 8,808,687 B2 | 8/2014 | Humayun et al. |
| 8,877,489 B2 | 11/2014 | Tai et al. |
| 9,248,013 B2 | 2/2016 | Tai et al. |
| 9,642,940 B2 | 5/2017 | Tai et al. |
| 10,188,769 B2 | 1/2019 | Humayun et al. |
| 2002/0081726 A1* | 6/2002 | Russell ............... C12N 5/0068 435/366 |
| 2002/0160509 A1 | 10/2002 | Reubinoff et al. |
| 2003/0054331 A1 | 3/2003 | Fraser et al. |
| 2003/0083646 A1 | 5/2003 | Sirhan et al. |
| 2003/0231791 A1 | 12/2003 | Torre-Bueno et al. |
| 2005/0031599 A1 | 2/2005 | Kooy et al. |
| 2005/0079616 A1 | 4/2005 | Reubinoff et al. |
| 2005/0106554 A1 | 5/2005 | Palecek et al. |
| 2005/0164383 A1 | 7/2005 | Reubinoff et al. |
| 2005/0214345 A1 | 9/2005 | Leng et al. |
| 2005/0260747 A1 | 11/2005 | Reubinoff et al. |
| 2006/0002900 A1 | 1/2006 | Binder et al. |
| 2006/0034891 A1 | 2/2006 | Lawin et al. |
| 2006/0078543 A1 | 4/2006 | Reubinoff et al. |
| 2006/0078545 A1 | 4/2006 | Carpenter et al. |
| 2006/0104957 A1 | 5/2006 | Yiu et al. |
| 2006/0149194 A1 | 7/2006 | Conston et al. |
| 2006/0234376 A1 | 10/2006 | Mistry et al. |
| 2006/0235430 A1 | 10/2006 | Le et al. |
| 2006/0282128 A1 | 12/2006 | Tai et al. |
| 2007/0106208 A1 | 5/2007 | Uber et al. |
| 2007/0128420 A1 | 6/2007 | Maghribi |
| 2007/0212777 A1 | 9/2007 | Reubinoff et al. |
| 2008/0140192 A1 | 6/2008 | Humayun et al. |
| 2008/0243224 A1 | 10/2008 | Wallace et al. |
| 2008/0299582 A1 | 12/2008 | Mandalam et al. |
| 2009/0004736 A1 | 1/2009 | Reubinoff et al. |
| 2009/0074832 A1 | 3/2009 | Zussman et al. |
| 2009/0075373 A1 | 3/2009 | Reubinoff et al. |
| 2009/0104695 A1 | 4/2009 | Shushan et al. |
| 2009/0117639 A1 | 5/2009 | Carpenter et al. |
| 2009/0123992 A1 | 5/2009 | Chin et al. |
| 2009/0130756 A1 | 5/2009 | Klann et al. |
| 2009/0270982 A1 | 10/2009 | Torres et al. |
| 2009/0291495 A1 | 11/2009 | Carpenter et al. |
| 2009/0305405 A1 | 12/2009 | Carpenter et al. |
| 2009/0306772 A1 | 12/2009 | Tao et al. |
| 2010/0068141 A1 | 3/2010 | Kaushal et al. |
| 2010/0093091 A1 | 4/2010 | Reubinoff et al. |
| 2010/0137510 A1 | 6/2010 | Seliktar et al. |
| 2010/0144033 A1 | 6/2010 | Mandalam et al. |
| 2010/0173410 A1 | 7/2010 | Thomson et al. |
| 2010/0189338 A1 | 7/2010 | Lin et al. |
| 2010/0203633 A1 | 8/2010 | Mandalam et al. |
| 2010/0211079 A1 | 8/2010 | Aramant et al. |
| 2010/0241060 A1 | 9/2010 | Roizman et al. |
| 2010/0272803 A1 | 10/2010 | Mistry et al. |
| 2010/0299765 A1 | 11/2010 | Klimanskaya et al. |
| 2010/0317101 A1 | 12/2010 | Mandalam et al. |
| 2011/0004304 A1 | 1/2011 | Tao et al. |
| 2011/0027787 A1 | 2/2011 | Chuck et al. |
| 2011/0053152 A1 | 3/2011 | Goldkorn et al. |
| 2011/0060232 A1 | 3/2011 | Lin et al. |
| 2011/0076320 A1 | 3/2011 | Coroneo |
| 2011/0091927 A1 | 4/2011 | Reubinoff et al. |
| 2011/0117062 A1 | 5/2011 | Klimanskaya et al. |
| 2011/0117063 A1 | 5/2011 | Klimanskaya et al. |
| 2011/0177594 A1 | 7/2011 | Shushan et al. |
| 2011/0189135 A1 | 8/2011 | Aharonowiz et al. |
| 2011/0236464 A1 | 9/2011 | Coffey et al. |
| 2011/0256623 A1 | 10/2011 | Thomson |
| 2012/0009159 A1* | 1/2012 | Humayun ............... A61K 35/30 424/93.7 |
| 2012/0083425 A1 | 4/2012 | George et al. |
| 2013/0137958 A1 | 5/2013 | Tai et al. |
| 2013/0143326 A1 | 6/2013 | Tai et al. |
| 2013/0144399 A1 | 6/2013 | Tai et al. |
| 2014/0134607 A1 | 5/2014 | Lin et al. |
| 2015/0032207 A1 | 1/2015 | Humayun et al. |
| 2015/0147377 A1 | 5/2015 | Humayun et al. |
| 2015/0147810 A1 | 5/2015 | Tai et al. |
| 2016/0014192 A1 | 1/2016 | Lim et al. |
| 2016/0310637 A1 | 10/2016 | Tai et al. |

FOREIGN PATENT DOCUMENTS

| | | |
|---|---|---|
| EP | 2593117 | 5/2013 |
| JP | 11-009297 | 1/1999 |
| JP | 5876045 | 3/2016 |
| WO | 2005/082049 | 9/2005 |
| WO | 2007/132332 | 11/2007 |
| WO | 2008/098187 | 8/2008 |
| WO | 2008/129554 | 10/2008 |
| WO | 2009/127809 | 10/2009 |
| WO | 2012/004592 | 1/2012 |
| WO | 2012/009377 | 1/2012 |
| WO | 2012/149468 | 11/2012 |
| WO | 2012/149480 | 11/2012 |
| WO | 2012/149484 | 11/2012 |

OTHER PUBLICATIONS

Lu et al. Highly Flexible, Transparent and Patternable Parylene-C Superhydrophobic Films With High and Low Adhesion; 2011 IEEE 24th International Conference on Micro Electro Mechanical Systems, 2011, pp. 1143-1146. (Year: 2011).*

(56) References Cited

OTHER PUBLICATIONS

PCT/US2011/043747 , "International Preliminary Report on Patentability", dated Jan. 24, 2013, 12 pages.
PCT/US2012/035654 , "International Preliminary Report on Patentability", dated Nov. 7, 2013, 7 pages.
Australian Application No. 2011279250, Office Action dated Jul. 5, 2013, 4 pages.
Australian Application No. 2015200823, Examination Report dated Jul. 17, 2015, 4 pages.
European Application No. 11807411.1, Extended European Search Report dated Dec. 16, 2013, 3 pages.
International Application No. PCT/US2012/035654, International Search Report dated Oct. 29, 2012, 4 pages.
Japanese Application No. JP 2013-519773, Office Action dated Jun. 8, 2015, 5 pages.
Tezcaner et al., "In Vitro Characterization of Micropatterned PLGA-PHBV8 Blend Films as Temporary Scaffolds for Photoreceptor Cells," J Biomed Mater Res vol. 86A, Issue 1, Oct. 23, 2007, pp. 170-181.
U.S. Appl. No. 14/314,994, Final Office Action dated Mar. 1, 2018, 19 pages.
U.S. Appl. No. 13/740,069, Final Office Action dated Jun. 19, 2015, 11 pages.
U.S. Appl. No. 13/740,069, Non-Final Office Action dated Aug. 28, 2014, 11 pages.
Wang et al., "Fabrication and characterization of a parylene-based three-dimensional microelectrode array for use in retinal prosthesis," Journal of Microelectromechanical Systems, IEEE Service Center, US, vol. 19, No. 2, Apr. 1, 2010, pp. 367-374.
12mm Transwell with 0.4 um Pore Polyester Membrane Insert, Retrieved from Internet: URL: http://catalog2. Corning. Com/Lifesciences/en- US/Shopping/PFProductdetails.aspx?productid=3460(Lifesciences ), Jun. 12, 2009.
U.S. Appl. No. 13/181,279, First Office Action Interview Summary dated Nov. 6, 2013, 35 pages.
U.S. Appl. No. 13/181,279, Pre-interview first office action dated Apr. 26, 2013, 7 pages.
U.S. Appl. No. 13/181,279, Restriction Requirement dated Oct. 1, 2012, 9 pages.
U.S. Appl. No. 13/355,426, Non-Final Office Action dated Oct. 25, 2013, 10 pages.
U.S. Appl. No. 13/355,426, Restriction Requirement dated May 23, 2013, 6 pages.
U.S. Appl. No. 13/740,069, Notice of Allowance dated Sep. 29, 2015, 7 pages.
U.S. Appl. No. 13/740,069, Restriction Requirement dated May 8, 2014, 7 pages.
U.S. Appl. No. 14/314,994, Non-Final Office Action dated Jun. 6, 2017, 21 pages.
U.S. Appl. No. 14/498,918, Final Office Action dated Oct. 19, 2015, 12 pages.
U.S. Appl. No. 14/498,918, Non-Final Office Action dated Mar. 3, 2015, 6 pages.
U.S. Appl. No. 15/004,796, Notice of Allowance dated Jan. 18, 2017, 10 pages.
U.S. Appl. No. 61/481,037, Biocompatible substrate for facilitating interconnections between stem cells and target tissues and methods for implanting same, Apr. 29, 2011, 149 pages.
International Application No. PCT/US2011/043747, International Search Report dated Jul. 24, 2012, 6 pages.
Algvere, Transplantation of RPE in Age-Related Macular Degeneration: Observations in 141 Disciform Lesions and dry RPE Atrophy, Graefe's Arch Clin Exp Ophthalmol, vol. 235, Issue 3, 1997, pp. 149-158.
Armstrong et al., The hydrodynamic radii of macromolecules and their effect on red blood cell aggregation, Biophys J., vol. 87, No. 6, Dec. 2004, pp. 4259-4270.
Binder et al., Transplantation of the RPE in AMD, Progress in Retinal and Eye Research, vol. 26, No. 5, Sep. 2007, pp. 516-554.
Chang et al., Cell and Protein Compatibility of Parylene-C Surfaces, Langmuir, vol. 23, vol. 23, 2007, pp. 11718-11725.
Chong et al., Management of inherited outer retinal dystrophies, present and future. Br J Ophthalmol, vol. 83, 1999, pp. 120-122.
DeBoer et al., Multiparameter Analysis of Primary Epithelial Cultures Grown on Cycloprore Membranes, Journal of Histochemistry and Cytochemistry, vol. 42, Issue 2, 1994, pp. 277-282.
Hannachi et al., Cell Sheet Technology and Cell Patterning for Biofabrication, Biofabrication, vol. 1, No. 2, Jun. 10, 2009, 13 pages.
Hsiao et al., Microfluidic system for formation of PC-3 prostate cancer co-culture spheroids, Biomaterials, vol. 30, 2009, pp. 3020-3027.
Huang et al., Stem cell-based therapeutic applications in retinal degenerative diseases, Stem Cell Reviews and Reports, Humana Press Inc., NY. vol. 7, No. 2, Sep. 22, 2009, pp. 434-445.
Jackson et al., Human retinal molecular weight exclusion limit and estimate of species variation, Invest Ophthalmol Vis Sci, vol. 44, No. 5, 2003, pp. 2141-2146.
Kannan et al., Stimulation of Apical and Basolateral VEGF-A and VEGF-C Secretion by 148 Oxidative Stress in Polarized Retinal Pigment Epithelial Cells, Molecular Vision, vol. 12, 2006, pp. 1649-1659.
Lavik et al., Fabrication of Degradable Polymer Scaffolds to Direct the Integration and Differentiation of Retinal Progenitors, Biomaterials, vol. 26, Issue 16, Jun. 2005, pp. 3187-3196.
Lee et al., Determination of human lens capsule permeability and its feasibility as a replacement for Bruch's membrane, Biomaterials, vol. 27, No. 8, Mar. 2006, pp. 1670-1678.
Liu et al., A 3-D microfluidic combinatorial cell culture array, IEEE Proc. of MEMS, 2009, pp. 427-430.
Lu et al., A 3-D parylene scaffold cage for culturing retinal pigment epithelial cells, Micro Electio Mechanical Systems (MEMS), 2012, pp. 741-744.
Lu et al., A study of the autofluorescence of parylene materials for 1-1TAS applications, Lab Chip, vol. 10, 2010, pp. 1826-1834.
Lu et al., Mesh-supported submicron parylene-C membranes for culturing retinal pigment epithelial cells, Biomed Microdevices, vol. 14, 2002, pp. 659-667.
Lu et al., Semipermeable parylene membrane as an artificial bruch's membrane, International Solid-State Sensors, Actuators and Microssytems Conference, 2011, pp. 950-953.
Lu et al., Thin collagen film scaffolds for reitnal epithelial cell culture, Biomaterials, vol. 28, 2007, pp. 1486-1494.
Lu et al., Ultrathin parylene-C semipermeable membranes for biomedical applications, IEEE International Micro Electio Mechanical Systems, Jan. 2011, pp. 505-508.
Morris et al., Cryopreservation of murine embryos, human spermatazoa and embryonic stem cells using a liquid nitrogen-free controlled rate freezer, Reproductive Biomedicine Online, vol. 13, vol. 3, 2006, pp. 421-426.
Neeley et al., A Microfabricated Scaffold for Retinal Progenitor Cell Grafting, Biomaterials, vol. 29, Issue 4, Feb. 2008, pp. 418-426.
Pereira-Rodrigues et al., Modulation of hepatocarcinoma cell morphology and activity by parylene-C coating on PDMS, PLoS One, vol. 5, No. 3, 2010, 13 pages.
Redenti et al., Engineering Retinal Progenitor Cell and Scrollable poly(glycerol-sebacate) 155 composites for Expansion and Subretinal Transplantation, Biomaterials, vol. 30, Issue 20, Apr. 9, 2009, pp. 3405-3414.
Redenti et al., Retinal Tissue Engineering using Mouse Retinal Progenitor Cells and a Novel Biodegradable, Thin-Film Poly(e-caprolactone) Nanowire Scaffold, J Ocul Biol. Dis Infor., vol. 1, Issue 1, May 22, 2008, pp. 19-29.
Roy et al., Silicon nanopore membrane technology for an implantable artificial kidney, Proc. of Transducers, 2009, pp. 755-760.
Sodha et al., A Microfabricated 3-D stem Cell Delivery Scaffold for Retinal Regenerative Therapy, Thesis, Master of Engineering in Biomedical Engineering, Massachusetts Institute of Technology, Jun. 2009.

(56) References Cited

OTHER PUBLICATIONS

Sodha et al., Microfabrication of a Three-Dimensional Polycaprolactone Thin-Film Scaffold for 158 Retinal Progenitor Cell Encapsulation, J Biomater Sci Polym Ed., vol. 22, Issue 4-6,, Jun. 21, 2011, pp. 443-456.

Stanzel et al., Culture of Human RPE from Aged Donors on a Potential Bruch's Membrane Prosthesis, Invest Ophthalmol Vis Sci, vol. 47. 2006.

Stanzel et al., Towards Prosthetic Replacement of Bruch's Membrane: Comparison of Polyester and Electrospun Nanofiber Membranes, Invest Ophthalmol Vis Sci, vol. 48, 2007.

U.S. Appl. No. 14/314,994, Notice of Allowance dated Sep. 11, 2018, 9 pages.

\* cited by examiner

TOP VIEW WITH CELLS

TOP VIEW

BOTTOM VIEW

TOP VIEW

BOTTOM VIEW

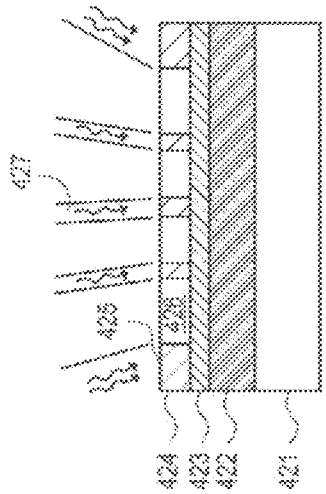
FIG. 4A
FIG. 4B
FIG. 4C
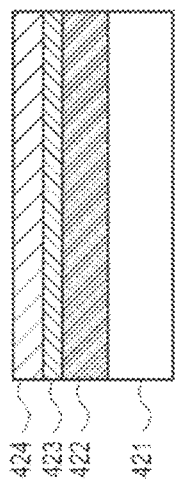
FIG. 4D
FIG. 4E
FIG. 4F
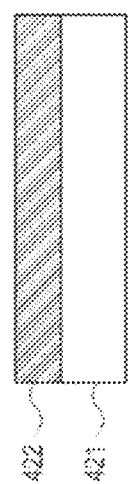
FIG. 4G
FIG. 4H
FIG. 4I

ULTRATHIN PARYLENE-C SEMIPERMEABLE MEMBRANES FOR BIOMEDICAL APPLICATIONS

CROSS REFERENCE TO RELATED APPLICATIONS

This application is a continuation of U.S. patent application Ser. No. 14/498,918, filed on Sep. 26, 2014 (abandonded), which is a continuation of U.S. patent application Ser. No. 13/355,426, filed on Jan. 20, 2012 (issued as U.S. Pat. No. 8,877,489), which claims the benefit of U.S. Provisional Patent Application No. 61/566,965, filed Dec. 5, 2011, and it is a continuation of U.S. patent application Ser. No. 14/314,994, filed on Jun. 25, 2014 (issued as U.S. Pat. No. 10,188,769), each of which is hereby incorporated by reference in its entirety for all purposes.

International Application No. PCT/US2011/043747, filed Jul. 12, 2011, and U.S. Provisional Application No. 61/481,037, filed Apr. 29, 2011, are hereby incorporated by reference in their entireties for all purposes.

STATEMENT AS TO RIGHTS TO INVENTIONS MADE UNDER FEDERALLY SPONSORED RESEARCH OR DEVELOPMENT

Not applicable.

BACKGROUND

1. Field of the Art

Embodiments of the present invention generally relate to biomedical membranes and, in particular, to ultrathin (e.g., between 0.01 µm to 5 µm thick) parylene C membranes that have exhibited permeability that is ideal for monolayer biological cell growth.

2. Description of the Related Art

Biological cells are often grown on membranes. For optimal growth of on on-membrane cell culture, the membranes must be permeable to nutrients (and waste from cells), such as proteins in serum. Membranes with pores that are large enough to allow proteins to flow through are used extensively in laboratories and are finding new applications as analysis equipment becomes smaller and more efficient.

Porous membranes are widely used in Micro Total Analysis System (µTAS) and Lab-on-a-Chip (LOC) applications, allowing chemical or biological reagents transportations and filtration. Among different types of membranes, commercially available track-etched porous membranes are one of the most popular choices, with various sizes of holes in submicron and micron (µm) ranges. Track etching involves heavy-ion bombardment of thin films and then chemical etching to reveal the tracks into holes.

Parylene, a generic name for members of a series of poly(p-xylylene) polymers, is generally biocompatible. Of the common types of parylene, parylene C is perhaps the most widely used in industry. Parylene C is sometimes referred to with a dash, i.e., "parylene-C," and sometimes is abbreviated as "PA-C." Its demonstrated bio-compatibility as a United States Pharmacopeial Convention (USP) Class VI biocompatible polymer makes it suitable for medical devices. However, it is not porous or considered permeable. In fact, it is used extensively in industry as a conformal coating for electronics and medical devices because it is water tight and essentially pinhole-free when chemical vapor deposited in extremely thin layers.

BRIEF SUMMARY

Generally, devices, systems, and methods for manufacturing a semipermeable parylene C membrane are disclosed. Parylene C—which has been found to be permeable to proteins in serum at ultrathin thicknesses (e.g., 0.01 µm to 5 µm thick)—is manufactured into a membrane having a smooth front side and tiny hills and valleys on the back side, such that it has a variable thickness. The hills and valleys, which can be stepwise-edged like a city skyline or histogram, can be manufactured using lithographic techniques.

One way of manufacturing such a membrane is to etch a relatively thick parylene film with tiny, through-hole perforations, lay it on a smooth substrate, and deposit an ultrathin layer of parylene over the perforated thick layer. The resulting parylene membrane is then peeled off of the substrate. The side of the membrane that was against the substrate is smooth, as the ultrathin layer of parylene covers the openings of the perforations. The opposite side of the membrane remains rough with hills and valleys because the ultrathin layer of deposited parylene was not enough material to fill in the etched perforations.

Embodiments of the present invention relate to a synthetic semipermeable membrane apparatus. The apparatus includes a membrane having a smooth front side, a back side, and spatially interspersed thin and thick regions between the smooth front side and the back side, the thin regions being a predetermined thickness of parylene, the predetermined thickness selected from a thickness between 0.01 µm to 5 µm, such as 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 µm. The thick regions comprise parylene or another material and are at least 2 times thicker than the predetermined thickness of the thin regions, and the interspersion of the thin and thick regions occur in a random or patterned array with an average feature size of about 1 µm to 10 µm, such as 1, 2, 3, 4, 5, 6, 7, 8, 9, or 10 µm.

Some embodiments relate to a synthetic semipermeable membrane apparatus, including a supporting film having a plurality of through perforations extending from a first side to an opposing, second side of the supporting film, and a 0.01- to 5-µm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 µm) thin parylene layer covering an opening of each perforation of the supporting film.

Some embodiments relate to a process for fabricating a synthetic semipermeable membrane. The process includes providing a supporting film having through perforations extending from a first side to an opposing, second side of the supporting film, laying the first side of the supporting film against a smooth substrate surface, depositing a 0.01- to 5-µm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 µm) thin parylene layer over the supporting film sufficient to cover a bottom of each perforation of the supporting film to form a membrane with a smooth first side, and removing the membrane from the smooth substrate surface.

Some embodiments relate to a method of using a synthetic semipermeable membrane, the method including providing a membrane that has a supporting film having a plurality of through perforations extending from a first side to an opposing, second side of the supporting film and a 0.01- to 5-µm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8 and 5.0 μm) thin parylene layer covering an opening of each perforation of the supporting film wherein the covered openings of the perforations are even with a surface of the first side of the supporting film, thereby forming a substantially smooth surface on the first side. The method further includes diffusing molecules through the membrane.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 4A illustrates depositing an initial thick parylene layer in a manufacturing process for a semipermeable membrane in accordance with an embodiment.

FIG. 4B illustrates a metal and photoresist application step in the manufacturing process of FIG. 4A.

FIG. 4C illustrates a photolithographic exposure step in the manufacturing process of FIG. 4A.

FIG. 4D illustrates an etching step in the manufacturing process of FIG. 4A.

FIG. 4E illustrates a peeling of the thick layer step in the manufacturing process of FIG. 4A.

FIG. 4F illustrates an attachment of the thick layer to another substrate in the manufacturing process of FIG. 4A.

FIG. 4G illustrates deposition of an ultrathin layer of parylene in the manufacturing process of FIG. 4A.

FIG. 4H illustrates the completed membrane removed from the second substrate in the manufacturing process of FIG. 4A.

FIG. 4I illustrates the membrane being used to grow a monolayer of cells after the manufacturing process of FIG. 4A.

DETAILED DESCRIPTION

Figure 1A:
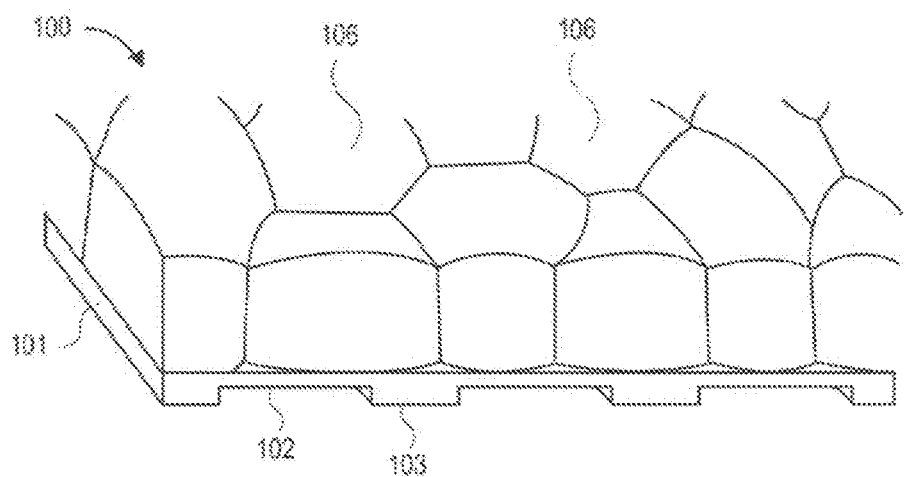
FIG. 1A is an oblique, cut-away top view of a semipermeable membrane growing a monolayer of cells in accordance with an embodiment.

Generally, devices, systems, and methods for manufacturing a semipermeable parylene C membrane are disclosed. A membrane with ultrathin (e.g., 0.01 μm to 5 μm thick) parylene regions is arranged to have a smooth side and a spatially variable thickness. The smooth side can be used to grow a monolayer of cells, while the bumps or undulations on the second side prevent cell growth on the second side. The ultrathin portions of the parylene are permeable to protein-sized molecules but impermeable to cells, which are on the order of 4 μm (for tiny photoreceptor rod and cone cells of the retina) to greater than 20 μm. The thicker portions of the membrane, which are interspersed with the thin portions, make the membrane stronger, less prone to folding or undulating, and generally easier to handle for surgeons.

Prior art porous membranes have been found to have disadvantages. First, the fabrication of small holes (i.e., <0.1 μm) is difficult to perform reliably. Therefore, in some applications where the cut-off selective size of the particles has to be smaller than 0.1 μm, porous membranes usually are not capable for biological applications. Second, when used in on-membrane cell culture applications, the porous topology may disturb the adherence and morphology of biological cells. The nooks and crannies of the pores present a non-smooth, variable surface, which is suboptimal for the growth of even cell monolayers. This can make the in vitro cultured cells very different from cells growing in their in vivo natural environment.

Materials that are naturally semipermeable are known, such as collagen and polydimethylsiloxane (PDMS). However, the surfaces of these semipermeable materials are often sponge-like. They are often not biocompatible, so they are not proper for implantation applications. Furthermore, they are difficult to reliably pattern into desired shapes and designs.

Parylene (including all the parylene derivatives such as parylene N, C, D, HT, AM, A, etc.) has been shown to be a superior biocompatible material, but it is usually used as a protective coating to prevent harmful large molecules from going through it. The inventors have not only determined how to use parylene as a permeable material, but they have also performed an in-depth study of the permeability of ultrathin parylene C to optimize the "thickness design" of parylene semi-permeable membranes. It has been found that parylene is permeable below some thicknesses, and the thinner the parylene, the more permeable it is. Furthermore, it is proposed that parylenes with thicknesses from 0.01 μm to 5 μm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 μm) can readily be used as semipermeable membranes in medical applications when coupled with thicker frames and supporting films.

Technical advantages of some of the embodiments are many. The smooth surface of the front side of a membrane is advantageous for cell growth than rough or spongy surfaces. The thin parylene areas allow nutrients and cell waste to pass through the membrane, while the thick areas give mechanical support and rigidity so that the membrane is less prone to tearing, folding, undulating, etc. during implantation. The thickness of the ultrathin parylene can be scaled for growing any cell type in a monolayer for implantation in the body. For example, retinal pigment epithelium (RPE) can be grown in a monolayer on the membrane. Cartilage trabeculae, heart muscle, and other cells can be grown in a monolayer as well. Besides facilitating in vitro perfusion cell culture, semipermeable parylene-C membrane also has use in the in vivo replacement of a Bruch's membrane in the eye for age-related macular degeneration. Bruch's membrane allows the passage of molecules with MW below 75 kDa.

An embodiment may be able to replace impaired human semipermeable tissue membranes anywhere in the human body, not just the Bruch's membrane. For example, the human lens capsule and collagen film can use parylene C membranes thinner than 0.30 μm.

As a proof of design, ultrathin parylene C membranes with thicknesses ranging from 0.15 μm to 0.80 μm have been experimentally verified. At least four different thicknesses (i.e., 0.15 μm, 0.30 μm, 0.50 μm, and 0.80 μm) of parylene C membranes manufactured on perforated support films were subject to diffusion studies using fluorescein isothiocyanate (FITC)-dextran molecules of different molecular weights (MWs) at body temperature (37° C.; 98.6° F.). A diffusion coefficients for each of five molecules (i.e. 10 kDa, 40 kDa, 70 kDa, 125 kDa, and 250 kDa) was obtained by fitting concentration-time curves into the equation:

$$C_2 = \frac{C_0 V_1}{V\left(1 - \exp\left(-\frac{Dt}{\tau h}\right)\right)} \quad \text{Eqn. 1}$$

where $$\tau = \frac{\left(V_1 + \frac{A_{eff} h}{2}\right)\left(V_2 + \frac{A_{eff} h}{2}\right)}{A_{eff} V} \quad \text{Eqn. 2}$$

where $C_0$ is the initial concentration on a first side of the membrane, $C_2$ is the concentration on the second side of the membrane (where $C_2$ at the start of each experiment is 0), $V_1$ and $V_2$ are the volumes of liquid on the respective sides of the membrane and $V=V_1+V_2$ (i.e., the total volume), h is the thickness of the ultrathin regions of the membrane (i.e., 0.15 μm, 0.30 μm, 0.50 μm, and 0.80 μm), and $A_{eff}$ is the effective area of the ultrathin portion of the membrane.

Because the membrane's thick regions were 20-μm diameter holes with a center-to-center spacing of 30 μm, $A_{eff}$ for all the tested membranes is:

$$A_{eff} = \frac{\pi (0.10 \ \mu m)^2}{0.30 \ \mu m \times 0.30 \ \mu m} \quad \text{Eqn. 3}$$

After obtaining the diffusion coefficients, the theoretical MW exclusion limit was then calculated for each thickness of film by extrapolating the linear relationship between the diffusion coefficients and the natural log of MW (i.e., ln(MW)) to a diffusion coefficient of zero. The results of this calculation are tabled in Table 1. Also tabled are respective exclusion radiuses (and diameters), calculated from the MWs of the FITC-dextran molecules.

TABLE 1

| Thickness (μm) | Exclusion MW (kDa) | Exclusion radius (μm) | Exclusion diameter (μm) |
| --- | --- | --- | --- |
| 0.15 | 1,302 | 0.02560 | 0.05120 |
| 0.30 | 1,008 | 0.02262 | 0.04524 |
| 0.50 | 291 | 0.01239 | 0.02478 |
| 0.80 | 71 | 0.0625 | 0.01250 |

Determining exclusion diameters of certain thicknesses of parylene is only part of the solution. While an ultrathin material may work in a laboratory, it may not be suitable in real-world situations.

Working with extremely thin parylene is difficult. To facilitate and strengthen the mechanical bending, stretching, and handling of ultrathin parylene, a thick supporting substrate design is disclosed. The supporting substrate is preferably thicker (e.g., 1-30 μm) than the ultrathin layers, such as two times as thick as the ultrathin layer. It can have various geometries, such as a mesh, net, pore, etc. geometry.

Further, a new substrate having an ultrathin parylene membrane with its back filled with some extremely permeable materials, such as silicone or hydrogels, is proposed for certain applications.

U.S. Patent Application Publication No. 2011/0236461 A1 to Coffey et al., published Sep. 29, 2011 (hereinafter "Coffey"), describes a polymer membrane for supporting the growth of retinal pigmented epithelial (RPE) cells in the human eye. Coffey discloses membrane pores between 0.2 μm and 0.5 μm in diameter (Coffey paragraph [0009]). The pore diameters in Coffey are substantially larger than exclusion diameters present in parylene C at the 0.01- to 5-μm thicknesses presented in this application (e.g., 0.0512 μm diameter; see Table 1). Furthermore, Coffey teaches that its membrane is preferably made from a hydrophilic polymer, such as polyester (see, e.g., Coffey paragraphs [0024] and [0043]), where parylene is characteristically hydrophobic.

The figures will be used to further describe aspects of the application.

Figure 1B:
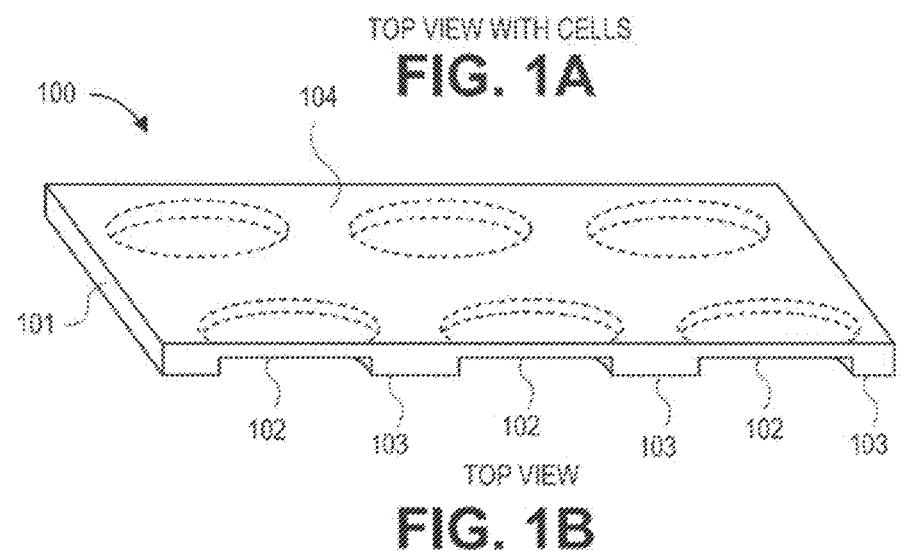
FIG. 1B is an oblique, cut-away top view of the semipermeable membrane of FIG. 1A without the cells.
Figure 1C:
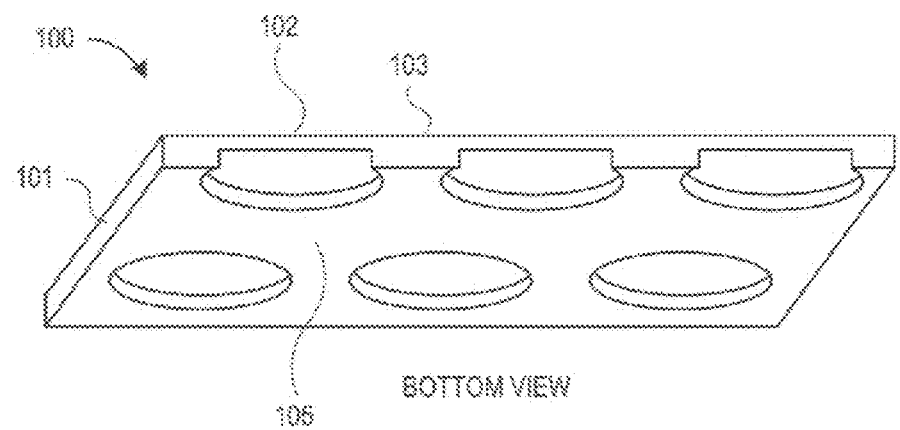
FIG. 1C is an oblique, cut-away bottom view of the semipermeable membrane of FIG. 1B.

FIGS. 1A-1C are oblique, cut-away views of a semipermeable membrane in accordance with an embodiment. FIG. 1A shows cells 106 growing on top of the membrane, while FIG. 1B omits the cells. FIG. 1C shows a bottom view of the membrane.

Biocompatible membrane system 100 includes membrane 101 having a front, top side 104 and a back, bottom side 105. Orientation terms of "front," "top," "back," "bottom," etc. are for the convenience of the reader and are not limiting as to absolute orientation. Front side 104 is smooth, having no salient protrusions or recesses that inhibit the natural formation of cells growing as a monolayer. Back side 105 is relatively rough, inhibiting or reducing the growth of cells.

Membrane 101 includes thin regions 102 interspersed with thick regions 103. In this embodiment, thick regions 103 are substantially contiguous with one another, and thin regions 102 comprise cylindrical recesses in the membrane. Thin regions 102 are interspersed in a regular, grid-like patterned array on membrane 101. In some embodiments, a random array, as opposed to one with a recognizable pattern, can be interspersed on the membrane. Embodiments having a combination of patterned and random arrays are also contemplated.

On front side 104, thin regions 102 flow cleanly with thick regions 103 to form a smooth surface as shown in FIG. 1B. On back side 105, thin regions 102 abruptly change to the plateaus of thick regions 103, forming a rough surface.

The thin regions are of a predetermined thickness, predetermined based on a permeability desired. For example, to allow proteins having a molecular weight of 70 kDa or smaller to flow through while inhibiting molecules having a molecular weight of over 100 kDa, the thickness of the thin regions can be engineered to be 0.80 μm thick (see Table 1).

The thick regions can be 2, 3, 4, 5, or 10 (and gradations in between) or more times thicker than the thin sections. Their increased thickness allows the entire membrane to be more easily handled. In the exemplary embodiment, thick regions 103 are 3 times the thickness of thin regions 102. In certain applications, thicknesses of more than 6 μm may be unwieldy. In some other cases, thick region thicknesses between 1 μm and 30 μm (such as 2, 3, 4, 5, 6, 7, 8, 9, 10, 11, 12, 13, 14, 15, 16, 17, 18, 19, 20, 21, 22, 23, 24, 25, 26, 27, 28, and 29 μm) thick can be used.

In other embodiments, the thin regions can be substantially contiguous with one another, with the thick regions comprising protrusions from the back side of the membrane. That is, instead of a bunch of holes as shown in FIG. 1C, there can be a bunch of mounds or other protrusions from an otherwise thin membrane.

"Substantially contiguous" regions include those that are flat with respect to each other without barriers or whose barriers are less than 10, 15, 20, or 25% of the respective regions' widths or as otherwise known in the art.

Figure 2A:
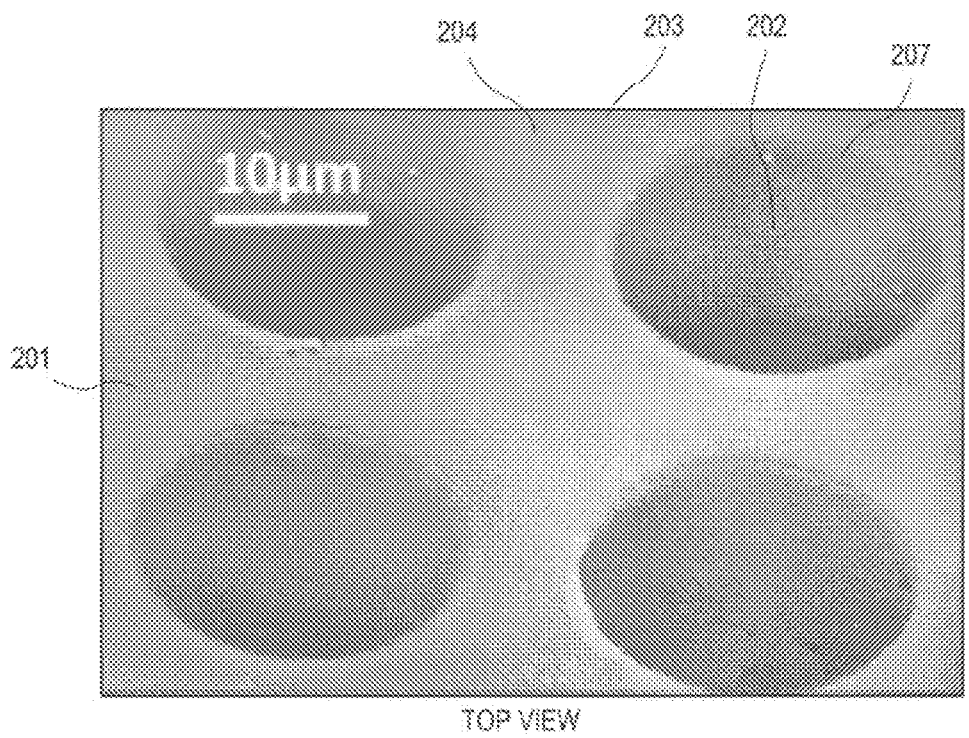
FIG. 2A is a scanning electron microscope (SEM) image of a top side of a semipermeable membrane manufactured in accordance with an embodiment.
Figure 2B:
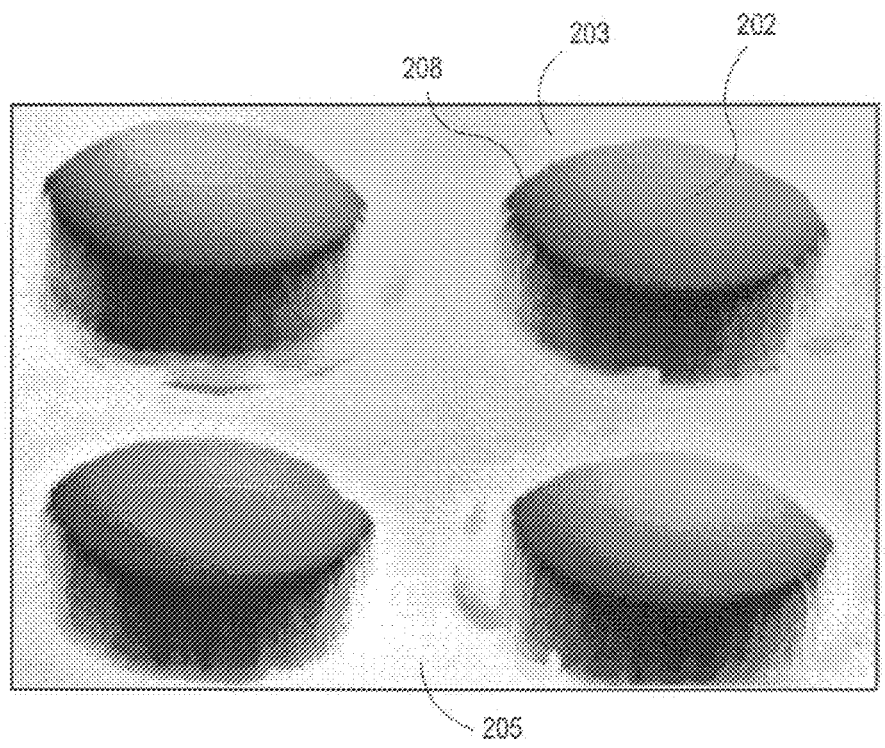
FIG. 2B is a scanning electron microscope (SEM) image of a bottom side of the semipermeable membrane of FIG. 2A.

FIGS. 2A-2B are scanning electron microscope (SEM) images of top and bottom sides of a semipermeable membrane manufactured in accordance with an embodiment.

In FIG. 2A, thin regions 202 of membrane 201 are almost transparent as seen from top side 204. They exhibit a drum-head like appearance, stretching over openings 207 in thick regions 203. Thicknesses of between 0.1 μm to 10 μm are considered to be a good range for many biological cells, allowing diffusion of proteins in serum to flow through the membrane. Thicknesses between 0.15 μm to 0.8 μm have been studied in depth. Thick regions of 3 μm to 4 μm thick allow a surgeon to manipulate the membrane with less chance of tearing, fold back, or undulation.

In FIG. 2B, recess 208 appears as a hole in thick region 203, bottoming out with thin region 202. The walls of recess 208 have been coated with an ultrathin layer of parylene to approximately the same thickness as the thin regions 202 as a result of a chemical vapor deposition (CVD) process described below.

Figure 3:
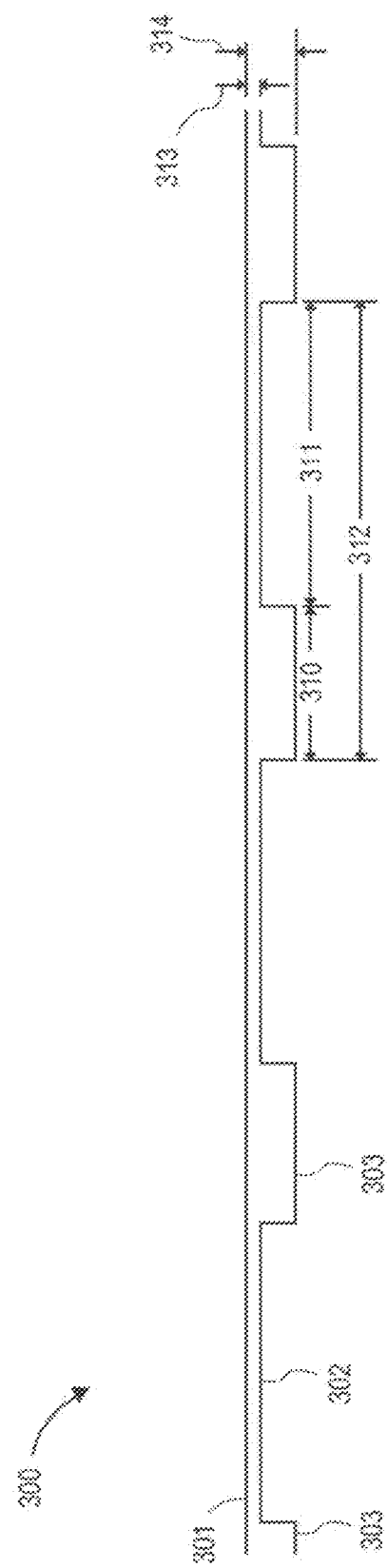
FIG. 3 is a side, elevation view of a semipermeable membrane in accordance with an embodiment.

FIG. 3 is a side, elevation view of a semipermeable membrane in accordance with an embodiment. Substrate 300 includes membrane 301 with thick regions 303 interspersed with repeating thin regions 302. Average feature size 310 of the plateaus between the repeating thin regions is about 10 μm (e.g., 7, 8, 9, 10, 11, or 12 μm). The thin regions are about 20 μm (17, 18, 19, 20, 21, or 22 μm) in diameter. The average, edge-to-edge (or center-to-center) pitch 312 is 30 μm (e.g., 26, 27, 28, 29, 30, 31, 32 μm). Thin region thickness 313 is 1 μm, while thick region thickness 314 is 3-4 μm. This spacing has been found to inhibit or reduce growth of cells that are about 20 μm in length.

FIGS. 4A-4H illustrate a manufacturing process for a semipermeable membrane in accordance with an embodiment.

As shown in FIG. 4A, an 8-μm thick supporting film 422 of parylene C is deposited on a cleaned, HMDS- (hexamethyldisilazane- or hexamethyldisiloxane-) treated silicon substrate 421. As shown in FIG. 4B, aluminum 423 is deposited on the parylene C supporting film 422 as an etching mask, followed by photoresist layer 424. As shown in FIG. 4C, photoresist layer 424 is illuminated in a random or patterned array using light 427. The photoresist becomes insoluble in regions 425 and soluble in regions 426. Soluble photoresist 426 is then washed away. As shown in FIG. 4D, wet-etching and reactive-ion etching (RIE) is used to etch 20 μm-diameter holes through supporting film 422 down to silicon substrate 421, to create array 428.

As shown in FIG. 4E, the now-perforated parylene layer 422 is removed from silicon substrate 421. As shown in FIG. 4F, perforated parylene layer 422 is attached to a different HDMS-treated silicon substrate 431. As shown in FIG. 4G, ultrathin parylene C film 429 (e.g., 0.15 μm to 0.80 μm thick) is then deposited on supporting film 422. The chemical vapor deposition (CVD) process results in a thin layer of parylene coating the walls as well as the bottom of the recesses. As shown in FIG. 4H, the completed membrane is peeled off, reversed and treated with $O_2$ plasma. The entire membrane, including both its thick and thin sections, is parylene, such as parylene C.

Manufactured membrane 401 has front side 404 (on the bottom in the figure) and back side 405 (on the top in the figure). Thin sections 402 are interlaced with thick sections 403 in pattern 428.

FIG. 4I illustrates membrane 401 being used to grow a monolayer of cells. The membrane has been rotated so that front side 404 faces up and back side 405 faces down. Cells 406 grow on smooth, front side 404 of membrane 401. Cells can be grown on the membrane in any orientation.

Figure 5:
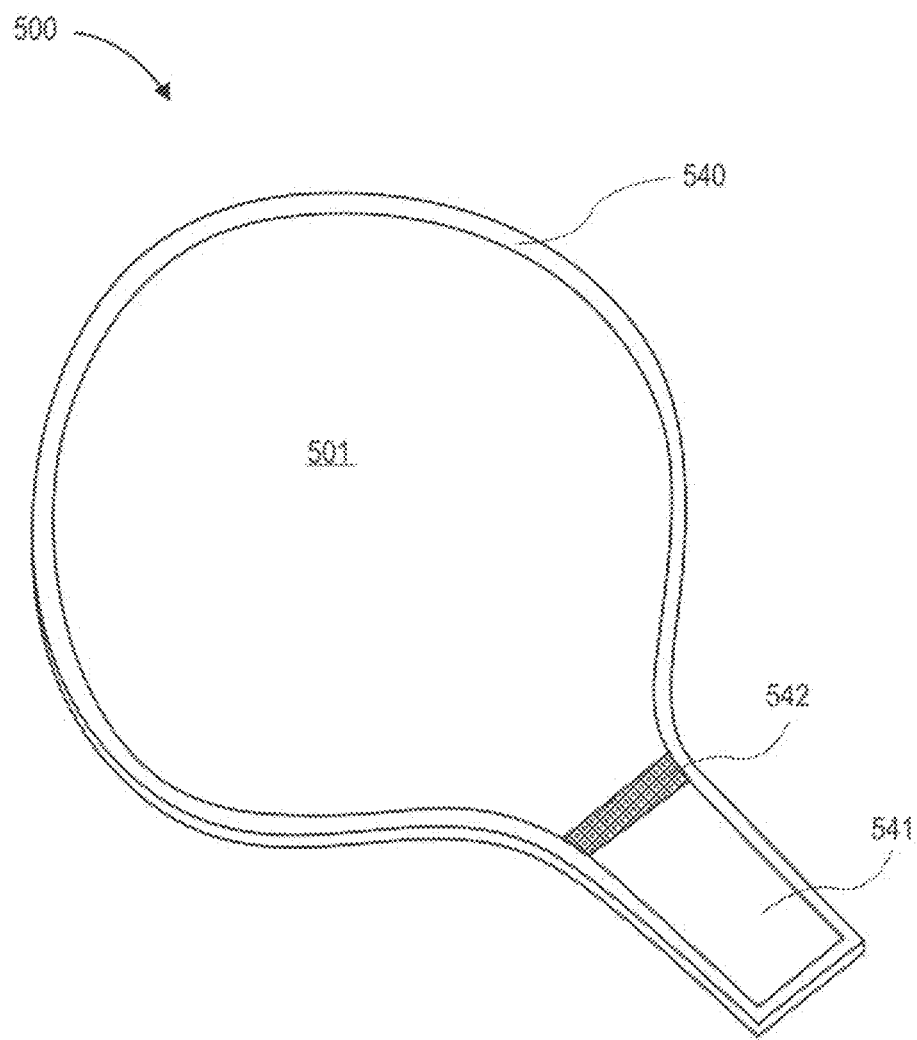
FIG. 5 illustrates an implantable membrane in accordance with an embodiment.

FIG. 5 illustrates an implantable membrane in accordance with an embodiment. Implantable membrane system 500 includes membrane 501 having tiny interlaced regions of ultrathin and thick biocompatible parylene. Frame 540 surrounds membrane 501 with a thick, relatively sharp edge that prevents or retards cells from migrating from a front, smooth side of the membrane to the back. Not only does frame 540 prevent or retard cells from migrating, but the relatively pointy and sharp edges of the rough side of the membrane prevents cells from gaining a foothold on the back side of the membrane. In this way, a surgeon can maximize the healthy monolayer growth of cells on one side of the membrane while minimizing undesirable cells on the back of the monolayer. This can be important in some applications, such as replacing the RPE behind the retina in the eye.

Tab 541 allows a surgeon's forceps or tool to hold the membrane, with cut-off section 542, or as otherwise described in U.S. Patent Application No. 61/481,037, filed Apr. 29, 2011.

Figure 6:
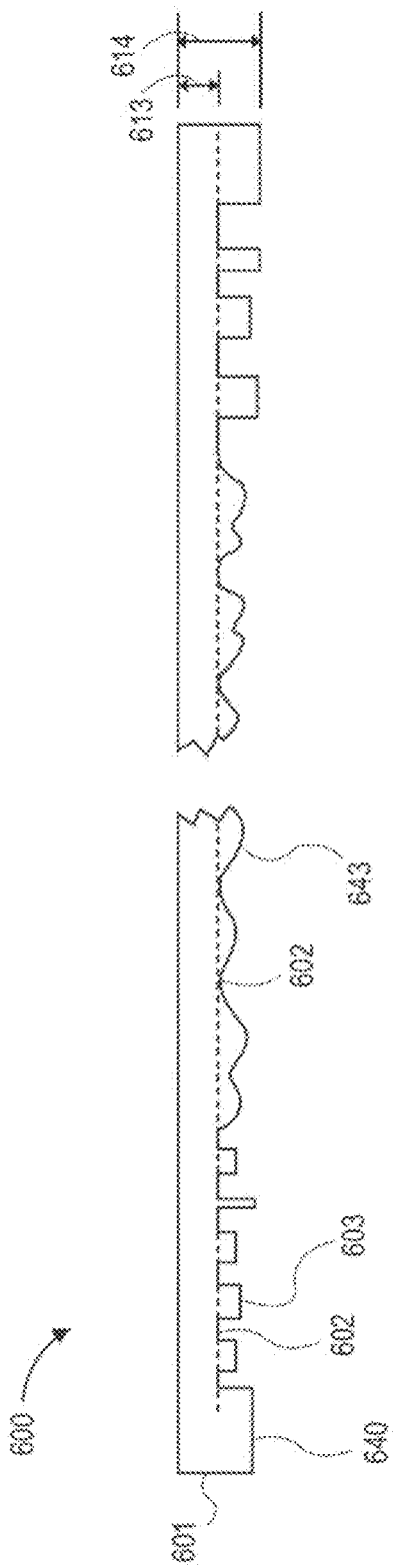
FIG. 6 is a side, elevation view of a semipermeable membrane with sharp and soft features in accordance with an embodiment.

FIG. 6 is a side, elevation view of a semipermeable membrane with sharp and soft features in accordance with an embodiment. Membrane system 600 includes membrane 601 with thin regions 602 of predetermined thickness 613.

Near circumference ring 640, membrane 601 includes thick regions 603 that have rectangular cross sections. Farther away from circumference ring 640, near the center of membrane 601, are thick regions 643 having rounded cross sections. Thick regions 603 have relatively sharp features with respect to thick regions 643, and thick regions 643 have relatively smooth features in comparison with thick regions 603.

Having relatively sharp regions near the circumference can retard or prevent cells that do happen to migrating around the edges of the membrane from growing on the membrane. Near the center, where there is less of a chance of cells migrating, the hills and valleys of the thick and thin regions can be smooth so that the membrane is better accepted during implantation and more compatible with the body.

Figure 7:
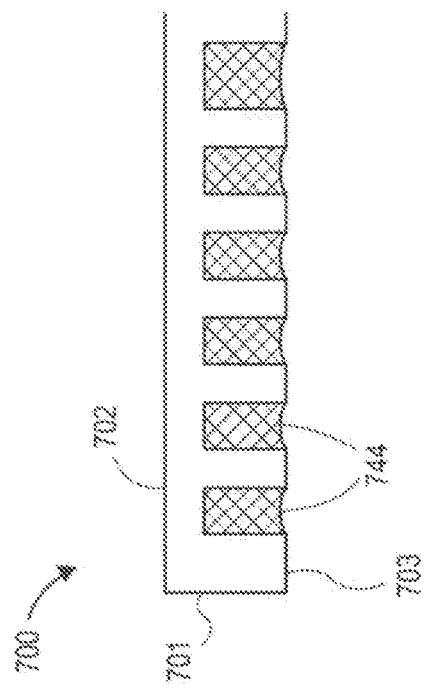
FIG. 7 is a side, elevation view of a semipermeable membrane with backfilled depressions in accordance with an embodiment.

FIG. 7 is a side, elevation view of a semipermeable membrane with backfilled depressions in accordance with an embodiment. In membrane device 700, membrane 701 has thin regions 702 and thick regions 703. Depressions on the bottom side where the thin regions exist are filled with a biocompatible, porous hydrogel 744, which smooths out the hills and valleys of the back side. This can be used in situations where a smooth surface for cell growth is desired on the back side of the membrane. Cells can grow on both sides of the membrane, as both sides have relatively smooth surfaces compared with the size of the cells to be grown.

Figure 8:
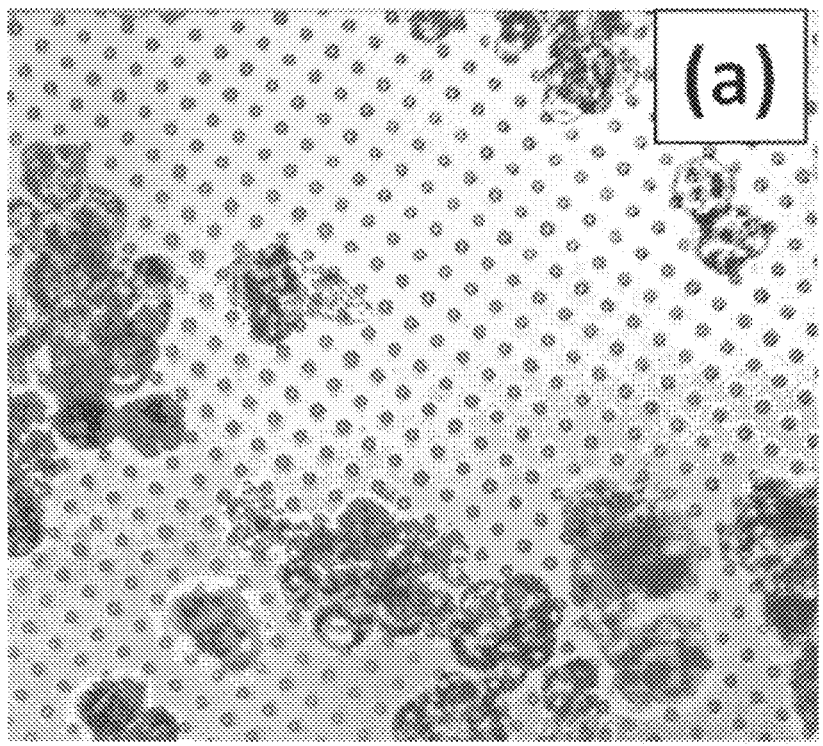
FIG. 8 is an image of cell growth on a porous membrane of the prior art.

FIG. 8 is an image of cell growth on a porous membrane of the prior art, showing H9-RPE (retinal pigment epithelial) cells cultured on a porous parylene-C membrane with oxygen plasma treatment. Note the clumpy adherence of cells, which is undesirable.

Figure 9:
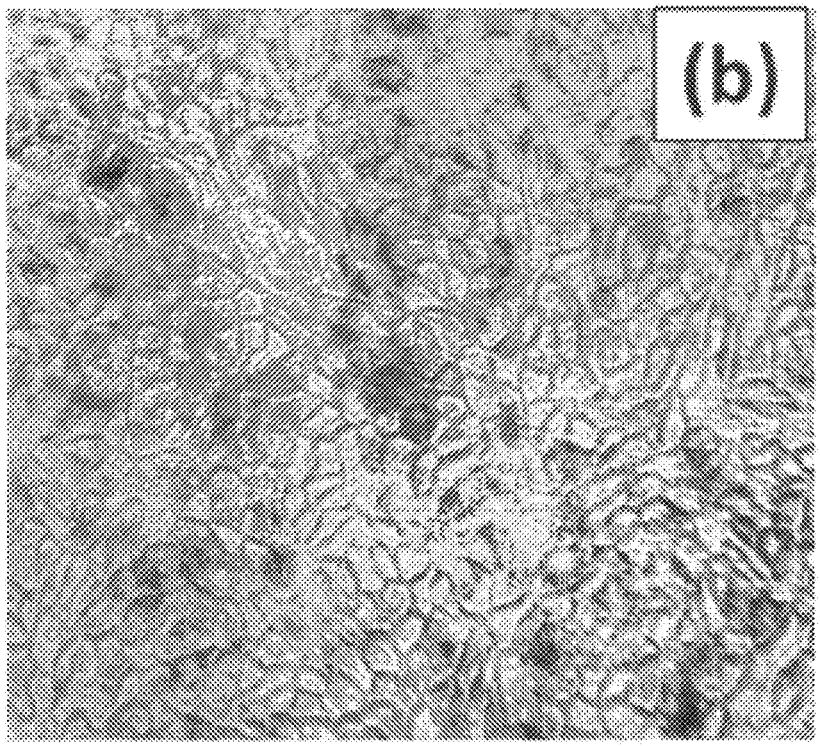
FIG. 9 is an image of cell growth on a semipermeable membrane in accordance with an embodiment.

FIG. 9 is an image of cell growth on a semipermeable membrane in accordance with an embodiment. The cell morphology is very different from that in FIG. 8. In FIG. 9, the cells grow in a relatively flat monolayer, having access to plenty of nutrients through the membrane and able to discharge cell waste through the membrane. The cells proliferated well, became confluent after ten days of culture, and showed clear signs of polarization. The cells also have desirable hexagonal boundaries.

Figure 10:
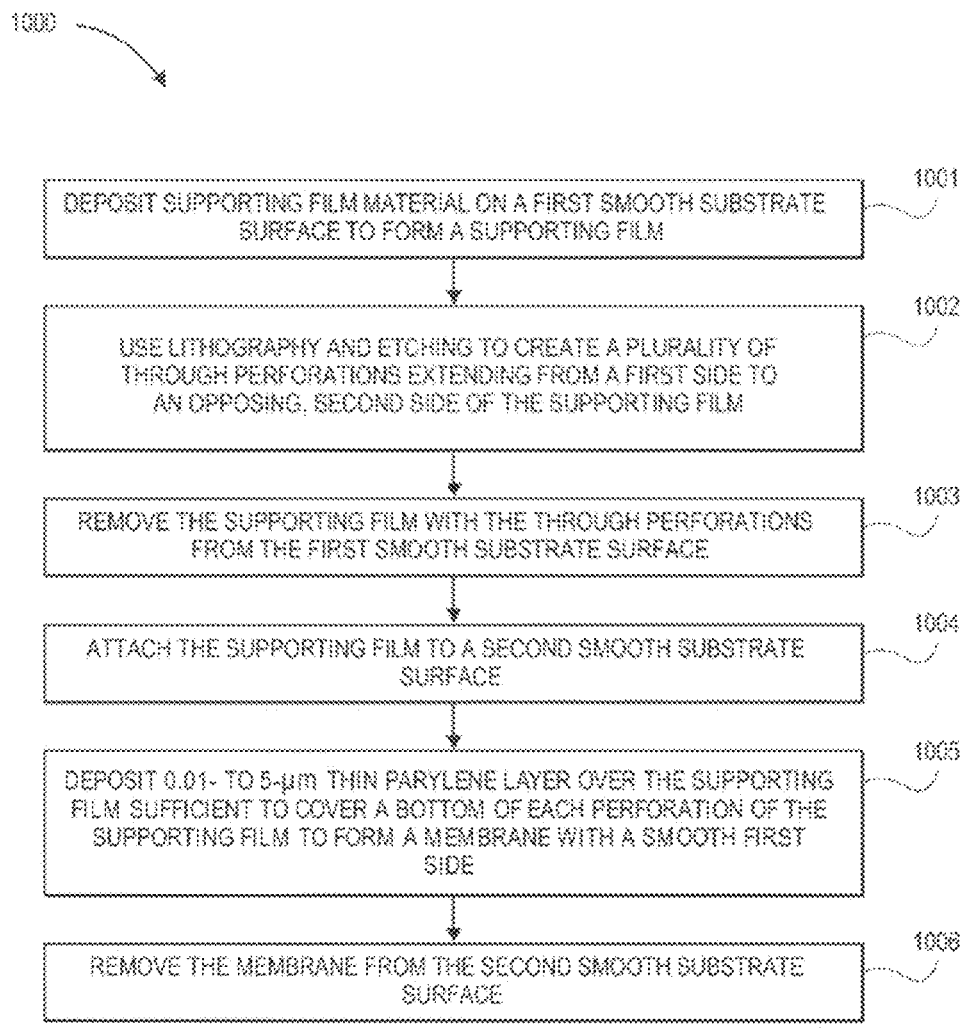
FIG. 10 is a flowchart illustrating a process in accordance with an embodiment.

FIG. 10 is a flowchart illustrating process 1000 in accordance with an embodiment. In operation 1001, a supporting film material is deposited on a first smooth substrate surface to form a supporting film. In operation 1002, lithography and etching are used to create a plurality of through perforations extending from a first side to an opposing, second side of the supporting film. In operation 1003, the supporting film with the through perforations is removed from the first smooth substrate surface. In operation 1004, the supporting film with the through perforations is attached to a second smooth substrate surface. In operation 1005, a 0.01- to 5-µm thin parylene layer is deposited over the supporting film sufficient to cover a bottom of each perforation of the supporting film to form a membrane with a smooth first side. In operation 1006, the membrane is removed from the second smooth substrate surface and readied for implantation.

Figure 11:
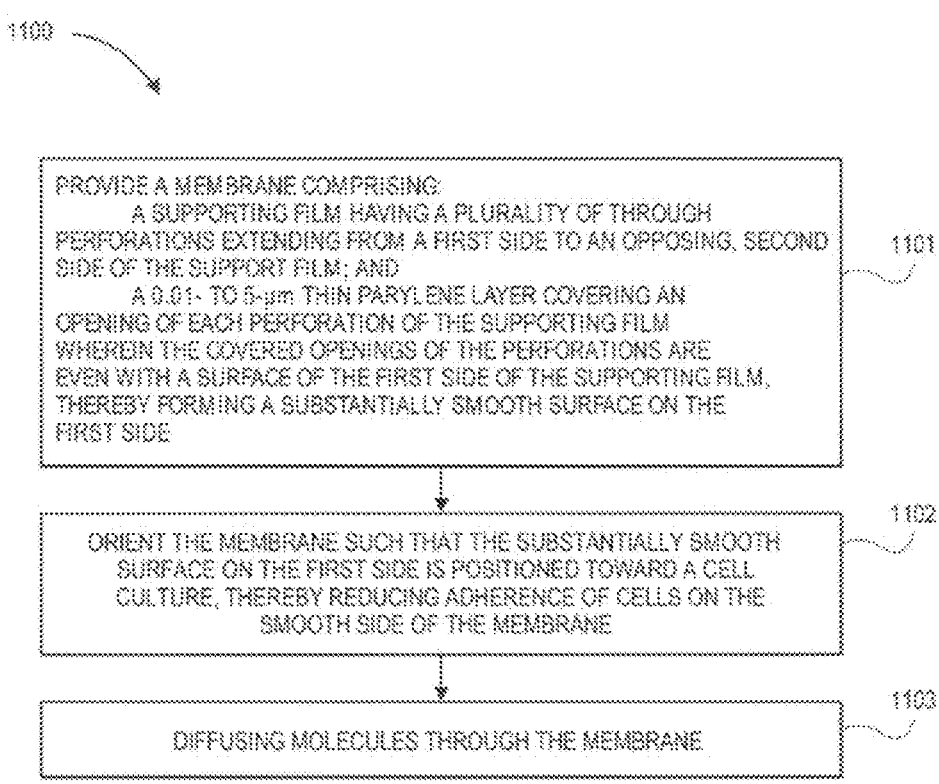
FIG. 11 is a flowchart illustrating a process in accordance with an embodiment.

FIG. 11 is a flowchart illustrating process 1100 in accordance with an embodiment. In operation 1101, a membrane is provided, the membrane comprising: a supporting film having a plurality of through perforations extending from a first side to an opposing second side of the supporting film; and a 0.01- to 5-µm thin parylene layer covering an opening of each perforation of the supporting film wherein the covered openings of the perforations are even with a surface of the first side of the supporting film, thereby forming a substantially smooth surface on the first side. In operation 1102, the membrane is oriented such that the substantially smooth surface on the first side is positioned toward a cell culture, thereby reducing adherence of cells on the smooth side of the membrane. In operation 1103, molecules are diffused through the membrane.

The invention has been described with reference to various specific and illustrative embodiments. However, it should be understood that many variations and modifications may be made while remaining within the spirit and scope of the following claims.

What is claimed is:

1. A synthetic semipermeable membrane for cellular therapy, the membrane comprising:
   a supporting film having through perforations extending from a first side to an opposing second side; and
   a parylene layer produced by chemical vapor deposition (CVD) of parylene over the perforated supporting film while the perforated supporting film is attached to a flat surface, the CVD sufficient to cover walls and a flat surface bottom of each perforation of the supporting film, and removing the supporting film with its parylene layer from the flat surface to form the membrane,
   wherein the membrane has a smooth front side with exposed areas of the parylene layer and is configured to facilitate the growth of a monolayer of cells and a rough back side configured to inhibit cell growth.

2. The membrane of claim 1, wherein the membrane is seeded with a plurality of cells.

3. The membrane of claim 2, wherein the plurality of cells form a monolayer on the membrane.

4. The membrane of claim 3, wherein the cells include heart muscle cells, cartilage trabeculae cells, or retinal pigment epithelium (RPE) cells.

5. The membrane of claim 1, wherein the membrane is composed of parylene C.

6. The membrane of claim 1, wherein the membrane has a plurality of thick regions that are two times as thick as a plurality of thin regions in the membrane.

7. The membrane of claim 1, wherein the perforations occur in a random array with an average feature size of about 1 micron to 10 microns.

8. A synthetic semipermeable membrane for cellular therapy, the membrane comprising:
   a smooth front side having exposed parylene layer areas and configured to facilitate the growth of a monolayer of cells, wherein the front side has a thickness of 0.15 microns to 0.5 microns and allows passage of molecules having a molecular weight of up to 1,302 kDa;
   a rough back side configured to inhibit cell growth and comprising a plurality of thin regions interspersed in a contiguous thick region, wherein the contiguous thick region provides mechanical support and rigidity to the membrane,
   the front and back sides having been formed from chemical vapor deposition (CVD) of parylene over a supporting film having perforations while the perforated supporting film is attached to a flat surface, the CVD of parylene at bottoms of the perforations forming the exposed parylene layer areas of the front side,
   wherein the plurality of thin regions are a plurality of cylindrical recesses in the membrane.

9. The membrane of claim 8, wherein the front side is configured to facilitate growth of a monolayer of retinal pigment epithelium (RPE) cells.

10. The membrane of claim 8, wherein the parylene is parylene C.

11. The membrane of claim 8, wherein a thickness of the contiguous thick region is constant.

12. The membrane of claim 11, wherein the thickness of the contiguous thick region is about 1 micron to about 30 microns.

13. The membrane of claim 12, wherein the thickness of the front side is about 0.15 microns to about 0.8 microns.

14. The membrane of claim 8, wherein the plurality of thin regions are interspersed in a grid-like pattern.

15. The membrane of claim 8, wherein the cylindrical recesses each have a diameter of at least about 10 microns.

16. A synthetic semipermeable membrane for cellular therapy, the membrane comprising:
   a smooth front side having exposed parylene layer areas and configured to facilitate the growth of a monolayer of cells, wherein the front side has a thickness of 0.15 microns to 0.5 microns and allows passage of molecules having a molecular weight of up to 1,302 kDa;

a rough back side configured to inhibit cell growth and comprising a plurality of thin regions interspersed in a contiguous thick region, wherein the contiguous thick region provides mechanical support and rigidity to the membrane, the front and back sides having been formed from chemical vapor deposition (CVD) of parylene over a supporting film having perforations while the perforated supporting film is attached to a flat surface, the CVD of parylene at bottoms of the perforations forming the exposed parylene layer areas of the front side, wherein the plurality of thin regions are interspersed in a grid-like pattern.

17. A synthetic semipermeable membrane for cellular therapy, the membrane comprising:

a smooth front side having exposed parylene layer areas and configured to facilitate the growth of a monolayer of cells, wherein the front side has a thickness of 0.15 microns to 0.5 microns and allows passage of molecules having a molecular weight of up to 1,302 kDa;

a rough back side configured to inhibit cell growth and comprising a plurality of thin regions interspersed in a contiguous thick region, wherein the contiguous thick region provides mechanical support and rigidity to the membrane, the front and back sides having been formed from chemical vapor deposition (CVD) of parylene over a supporting film having perforations while the perforated supporting film is attached to a flat surface, the CVD of parylene at bottoms of the perforations forming the exposed parylene layer areas of the front side, wherein the front side of the membrane is seeded with a plurality of cells.

18. The membrane of claim 17, wherein the plurality of cells form a monolayer on the front side of the membrane.

19. The membrane of claim 18, wherein the cells are retinal pigmented epithelium (RPE) cells.

20. The membrane of claim 17, wherein the plurality of thin regions are interspersed in a grid-like pattern.

* * * * *